United States Patent [19]

Akopov et al.

[11] Patent Number: 5,059,214

[45] Date of Patent: Oct. 22, 1991

[54] SURGICAL FORCEPS

[75] Inventors: Ernest M. Akopov; Elena N. Kapitanova, both of Moscow, U.S.S.R.

[73] Assignee: Vsesojuzny Nauchno-Issledovatelsky i Ispytatelny Institut Meditsinskoi Tekhniki, Moscow, U.S.S.R.

[21] Appl. No.: 328,157

[22] PCT Filed: May 26, 1988

[86] PCT No.: PCT/SU88/00123

§ 371 Date: Feb. 24, 1989

§ 102(e) Date: Feb. 24, 1989

[87] PCT Pub. No.: WO88/10097

PCT Pub. Date: Dec. 29, 1988

[30] Foreign Application Priority Data

Jun. 26, 1987 [SU] U.S.S.R. .............. 4268325

[51] Int. Cl.⁵ .............................................. A61B 17/28
[52] U.S. Cl. .................................. 606/207; 81/418
[58] Field of Search .............................. 606/205–207, 606/151, 157; 294/99.2; 81/418–420; 433/139

[56] References Cited

U.S. PATENT DOCUMENTS

| D. 246,190 | 10/1977 | Hodge | 606/207 |
|---|---|---|---|
| 2,796,065 | 6/1957 | Kapp | 606/207 |
| 2,842,132 | 7/1958 | Soltero et al. | 606/207 |
| 3,083,711 | 4/1963 | Ramsey | 606/207 |
| 3,101,715 | 8/1963 | Glassman | 606/207 |
| 3,503,397 | 3/1970 | Fogarty et al. | 606/207 |
| 3,515,139 | 6/1970 | Mallina | 606/207 |
| 3,815,607 | 6/1974 | Chester | 128/354 |
| 3,911,925 | 10/1975 | Tillery, Jr. | 606/151 |
| 4,475,544 | 10/1984 | Reis | 606/151 |
| 4,827,929 | 5/1989 | Hodge | 606/207 |

FOREIGN PATENT DOCUMENTS

| 2338686 | 1/1977 | France . |
| 141258 | 1/1961 | U.S.S.R. . |
| 180744 | 5/1966 | U.S.S.R. . |

OTHER PUBLICATIONS

Catalogue of the Firm Aesculap "Instrumente für Diagnostik, Kleine und Grosse Chirurgie, Urologie, Gynäkologie und Geburtshilfe", Band 1,9 Auflage p. 266, No. 3–21178; p. 267, No. B–21181; p. 329, No. E–295.

Primary Examiner—C. Fred Rosenbaum
Assistant Examiner—William W. Lewis
Attorney, Agent, or Firm—Fleit, Jacobson, Cohn, Price, Holman & Stern

[57] ABSTRACT

The surgical forceps are composed of two movably interconnected halves (1,2). Each of said halves terminates in an oblong jaw (4,5) having an effective portion (8) with a compressing surface (17,18) which is provided with alternately arranged prongs (21) and recesses (22) corresponding to the respective recesses (22) and prongs (21) on the opposite compressing surface of the other jaw. The prongs (21) and recesses (22) are arranged on at least one longitudinal edge of the compressing surface (17,18) the recesses (22) being open towards the outer surface (19 or 20) of the effective portion (8) of the jaws (4,5).

16 Claims, 4 Drawing Sheets

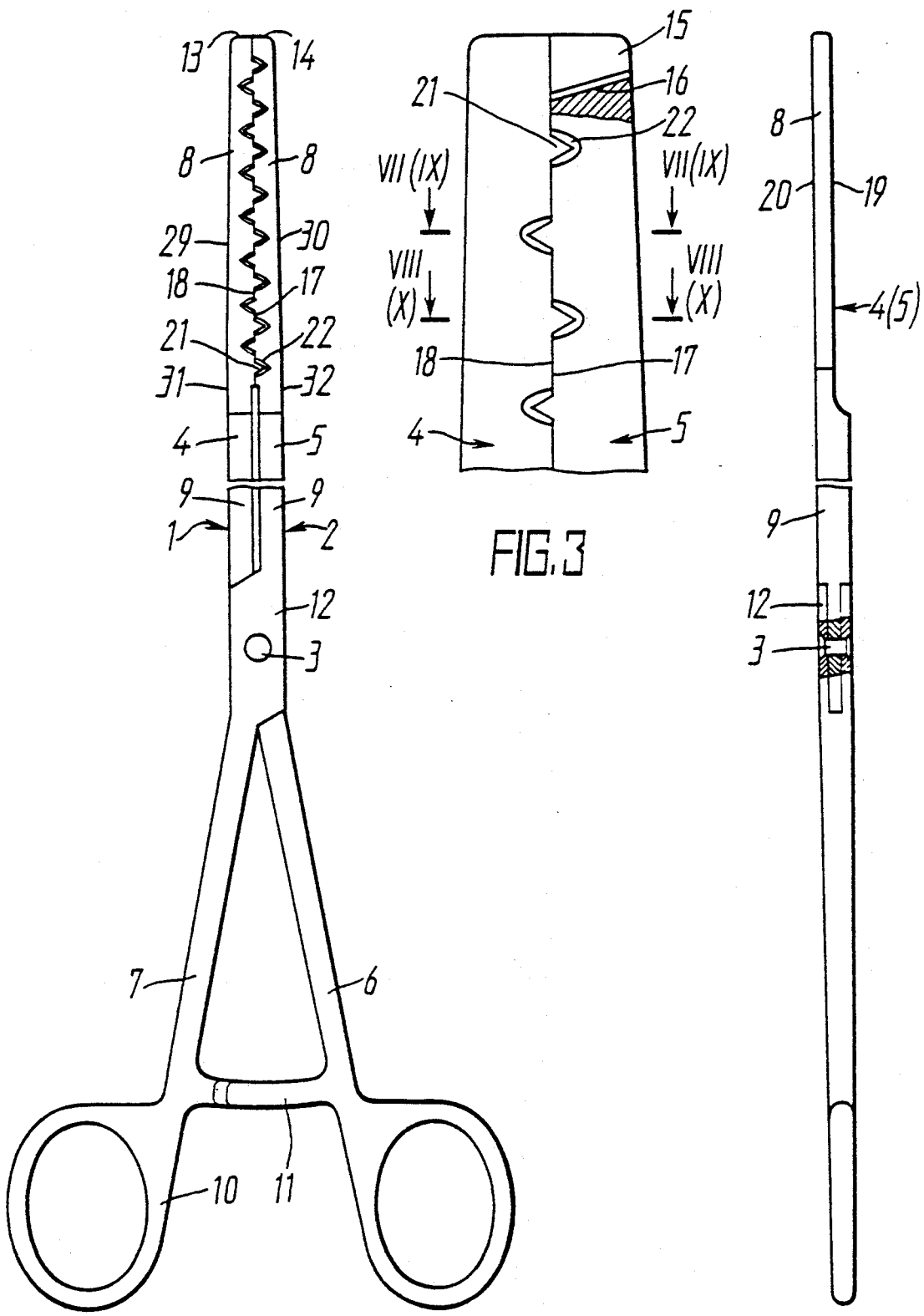

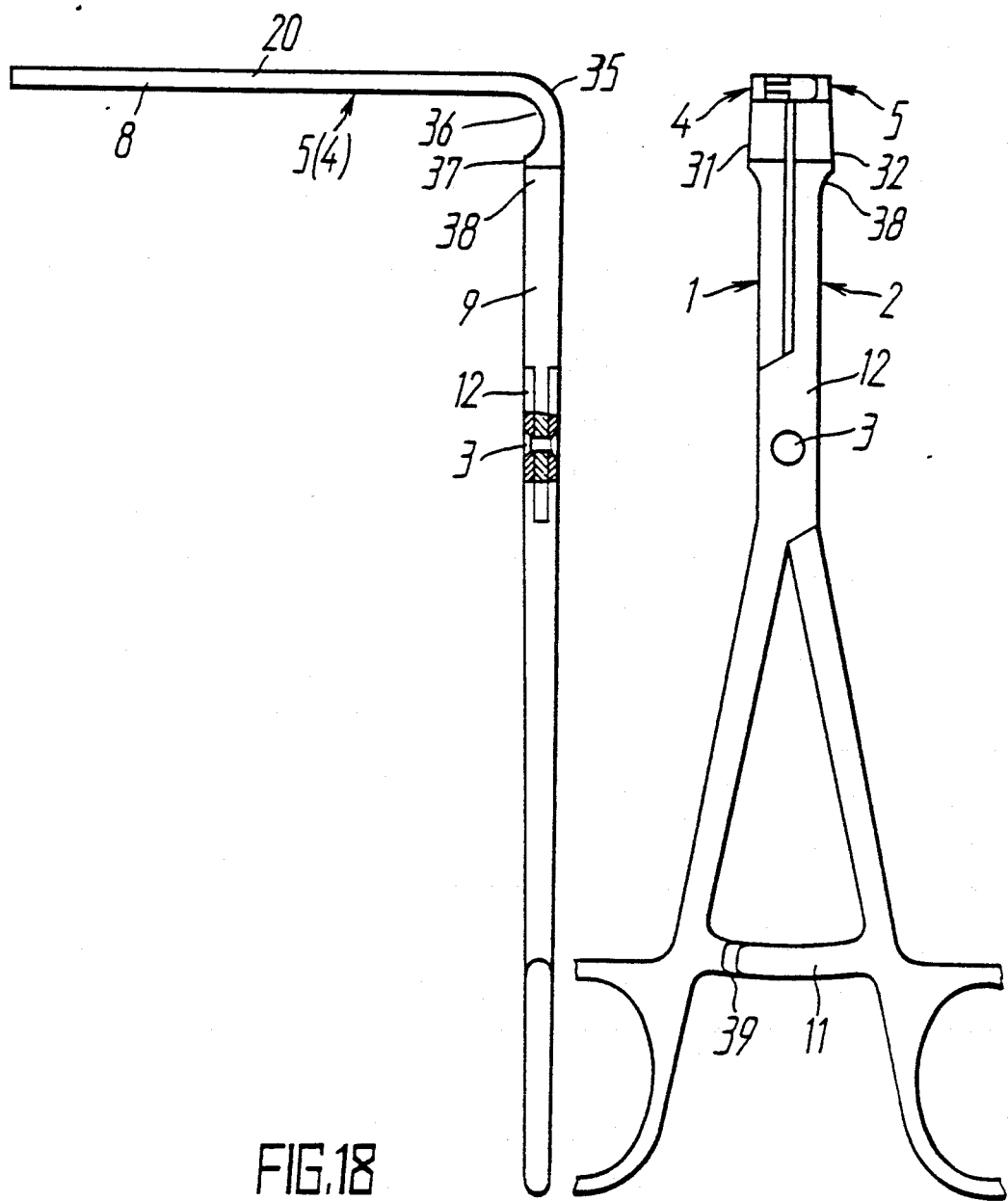

SURGICAL FORCEPS

FIELD OF THE ART

The present invention relates to medical engineering, namely, to surgical forceps for grasphing and holding tissues or organs during various manipulations in the operative wound in the course of most diverse surgical procedures, in particular, for reliable closuse of a cavity and holding the resected organ portion that has been severed after mechanical suture application with the aid of a suturing appliance, e.g., in the case of resecting of an intestine, the stomach or other organs of the abdominal and thoracic cavities.

PRIOR ART

Prior art surgical forceps for grasping and holding tissues or organs are known to comprise two halves movably interconnected and having oblong jaws with compressing (inner) and outer surfaces of the working (effective) portions. The forceps have serration situated on the compressing surface of the effective law portion (cf., e.g., a Catalogue of the firm Aesculap "Instrumente für Diagnostik, kleine und grosse Chirurgie, Urologie, Gynäkologie und Geburtshilfe", Band 1, 9 Auflage P. 226, No. B-21178), or longitudinal grooves or flutes provided on each jaw and so arranged that the grooves on one of the jaws are located opposite to the projections or lugs on the other jaw (cf. ibid., p. 267, No. B-21181 DF).

Serration and grooves-and-lugs are aimed at increasing the forces of adhesion of the surfaces of tissues or organs with the compressing surface of the effective jaw portion. However, such forceps fail to provide a reliable holding of tissues and organs in the forceps without their overcompression, which is causative of a traumatic lesion. The known forceps fail to prevent the compressed walls of organs from slipping off the forceps, especially when tensioning the tissues square with the forceps jaws. This is the case when, e.g., severing the resected portion of organs immediately at the forceps jaws after application of a mechanical suture with the aid of a surgical suturing appliance in the course of resection of organs. The possibility of escaping of the tissues clamped by the forceps off the latter during various manipulations involved in surgery is fraught with the danger of infecting the operative wound, since the cavity of the organ operated upon gets open so that the contaminated inner surface of the organ is brought in contact with the surrounding tissues, the infected contents flow out of the cavity, and hemostasis is disturbed. In order to increase the force of adhesion of the compressing surface of the forceps jaws with the tissues being handled, one has to increase the width of the jaws of the known forceps, which is not always possible due to specific conditions of a surgery, e.g., when the amount of tissues is insufficient for the forceps jaws to set to the working position. Besides, in order to provide a reliable fixation of the walls of the organ being operated upon, one whould increase the rigidity of the cantilivered jaws of the forceps, since it is not infrequently that the compression force applied to the walls of organs is to be very high so as to prevent their escaping from the jaws, which is the case when compressing and fixing the walls of the resected stomach portion in the course of gastrectomy. Thus, the forceps get bulky and have too wide and high jaws, which deteriorates their maneuvrability in the operatuve wound. When such forceps are used for compressing the organs and tissues that are to remain in the organism after surgery, these tissues might be overcompressed and necrosis might subsequently result.

Another prior-art forceps, such as, e.g., Price-Thomas (cf. the Catalogue of the firm Aesculap mentioned hereinabove, Item No. B-21182, p. 267) is made up of two halves movably interconnected and having oblong jaws with compressing and outer surfaces. A number of through perforations are made in the compressing surface of the effective portion of one of the jaws of the forceps along the centre line of said surface. The other jaw are provided with pointed cone-shaped lugs or prongs arranged likewise along the centre line of the jaw and adapted to engage the aforementioned perforations when the jaws are brought together.

However, practical application of the Price-Thomas forceps is inconvenient due to too great a width of the jaw effective portion. Through perforations in the jaws reduce substantially their rigidity, are in effect stress concentrators and, therefore, render the jaws unreliable, especially in the case of long-length jaws, which are liable to break during surgery when compressing massive solid walls of organs. That is why the jaws of the Price-Thomas forceps are to be made wide and short so that such forceps cannot be used for grasping and fixing tissues that have a relatively large length. Provision of the prongs only on one jaw provide reliable holding for only one side of the compressed walls of an organ, e.g., those of the stomach or large intestine, whereas the other wall situated on the side of the perforated jaw might escape from the forceps, with the result that the cavity of the organ will be opened and asepsis of the surgery by affected. To make grasping and holding of tissues more reliable it is necessary to increase the height of prongs so that both walls of a thick-walled organ should be pierced. However, the higher the prongs the lower their strength, the prongs are inconvenient in manipulations with the forceps, while the danger of inflicting traumatic lesions on the tissues operated upon and on the surrounding tissues, as well as on surgeon's hands. It should also be pointed out that small-diameter perforations arranged along the centre line of the jaws are in fact dirt accumulators and are inconvenient for cleaning.

More reliable from standpoint of reliable grasping and holding of both walls of the tissues operated upon is the heretofore-known Mikulicz forceps, Catalogue No. E-295 (cf. the aforementioned Catalogue of the firm Aesculap, p. 329). Unlike the above discussed forceps, the effective portion of each jaw has a number of prongs arranged along the jaw centre line and standing over the compressing jaw surface and facing the opposite jaw, and a number of through perforations so interposed between the prongs that the prongs of one jaw are situated against the perforations in the opposite jaw. Thanks to such a construction feature the Mikulicz forceps provide for reliable fixation of the both walls of tissues or organs compressed between the forceps jaws. However, it is due to specific construction features of the effective portion of the forceps jaws provided with prongs and through perforations arranged lengthwise the centre line of said jaws that said forceps feature too wide jaws which are inadequately strong and rigid. As a result, the forceps are wieldy, especially when the jaws have a considerable length, the forceps jaws require rather wide tissues to be set to the working position, the forceps are poorly maneuvrable in the operative wound, the jaws are liable to break, and the forceps feature but a short service life. Besides, through perforations and prongs arranged along the jaw centre line are inconvenient for cleaning.

The aforesaid disadvantages place limitations upon practical use of the known forceps in surgical practice, whenever it is necessary to reliably grasp and hold the walls of organs for a relatively long length, e.g., when compressing the resected portion of the organ operated upon after application of a mechanical suture with the aid of a suturing appliance. Moreover, the known forceps are inconvenient or inapplicable altogether whenever there is a deficit of tissues required for the forceps jaws to set on; they are unhandy and traumatizing during manipulations in a deep and narrow operative wound, which is the case, e.g., in proctology during manipulations in the small pelvis, in thoracic surgery during operations on the esophagus, in children's surgery, and the like.

DISCLOSURE OF THE INVENTION

It is an object of the present invention to provide such surgical forceps that would make it possible, due to appropriate shape and arrangement of the construction elements of the compressing surface of the effective jaw portion, to considerably enhance maneuvrability of the forceps in the operative wound and extend their service life, render their cleaning more convenient, and provide reliable grasping and holding of tissues and walls of organs.

Said object is accomplished due to the fact that in surgical forceps, composed of two movably interconnected halves, each of said halves terminating in an oblong jaw having an effective portion with a compressing surface, whereon provision is made for alternatingly arranged prongs and recesses, which correspond to the respective recesses and prongs on the compressing surface of the other jaw, according to the invention, the prongs and recesses are arranged on at least one longitudinal edge of the compressing jaw surface and the recesses open towards the outer surface of the jaw effective portion.

Such a construction arrangement of the forceps makes it unnecessary to arrange the fixing prongs and the respective through perforations along the centre line of the compressing surface of the effective jaw portion which is the case with the known forceps, thus reducing considerably (practically twofold or more) the width of the jaw effective portion while providing for reliable grasping and holding tissues and walls of organs of various thicknesses. Smaller width of the jaws and, hence, better maneuvrability of the forceps renders them applicable in hard-of-access places and the cases of a deficit of tissues required for setting the forceps to the working position, e.g., when compressing and excising, along the forceps jaws, the resected portion of the pharynx together with the larynx, following application of a mechanical suture to the pharynx with the aid of a suturing appliance during surgery for laryngeal carcinoma. Provision of the recesses that open towards the outer surface of the jaw effective portion rather than of those made as through or blind perforations (which is the case with the known analogues) which are in fact dirt accumulators and bad stress concentrators, makes it possible, other things being equal, to add to the strength of the jaws and rule out their breakage, to improve conditions of their postoperative cleaning, and cut down forceps maintenance time.

It is expedient that a part of the lateral prong surface be essentially an extension to the outer surface of the jaw effective portion. Such integration of said surfaces facilitates cleaning of the forceps and enables one to dispense with projections on the outer surface of the jaw effective portion, thus rendering possible a convenient and smooth travel of a scalpel over the effective portion of the jaws for dissecting the tissues held, e.g., between the forceps jaws compressing the walls of the resected organ portion and the suturing appliance when applying a mechanical suture to the organ being resected.

It is desirable that the surface of the recess should make part of the surface of a body of revolution so that the generatrix of said surface located in an axial section of the recess be inclined with respect to the outer surface of the jaw effective portion. It is thanks to such an embodiment of the forceps that the maximum strength of the jaw effective portion is ensured with a comparatively small width of the jaws, as well as their cleaning is facilitated, since the recesses have a continuous open corner-free surface featuring a free and unobstructed success for cleaning on the side of both the compressing and outer surfaces.

It is likewise expedient that, when provision is made for prongs and recesses along each longitudinal edge of the compressing surface of the jaw effective portion, the prongs and recesses arranged on one longitudinal edge should be displaced with respect to the prongs and recesses arranged along the opposite edge of the compressing surface of the jaw effective portion. Such a construction arrangement of the effective portion of the forceps jaws provides for uniform grasping and a more reliable fixation of tissues and walls of organs lengthwise their compression strip, and is favourable from the standpoint of strength and durability of the forceps jaws due to a displaced arrangement of the recesses on one longidutinal edge of the compressing surface with respect to the recesses on the other longitudinal edge. A displaced arrangement of the prongs on one longitudinal edge of the compressing surface with respect to the prongs on the other longitudinal edge renders cleaning of the compressing jaw surface more convenient, since such an arrangement provides for an easier access to the base of the prongs for their cleaning and makes dirt accumulation in that region less probable compared with the case where the prongs on both edges of the compressing surface would be arranged opposite to each other.

It is favourable that the effective portion of the jaws be much narrower than the remaining part thereof. Such a possibility is ensured due to the aforementioned construction features of the prongs and recesses of the forceps being disclosed and their position with respect to the compressing and outer surfaces of the jaw effective portion and relative to one another and in turn makes it possible to considerably reduce the width of tissues required for setting the forceps to the tissue compressing position, as well as renders the forceps more maneuvrable in the operative wound. Moreover, the aforesaid forceps construction, wherein the effective portion is much narrower than the other portion of the instrument makes it possible to use standard-size locking devices which is usually employed in forceps of other types, e.g., standard box-type locks. This, in turn, makes it possible to unify the construction elements of forceps of the various types, which simplifies their production.

The jaw effective portion may be made so that its height should increase from the end of the effective portion towards the base so that the height of the jaw effective portion at the base is expedient to exceed the height of the remaining part of the jaws. Thus, when compressing solid massive tissues and walls of organs featuring a great compressing length, this feature provides for high rigidity of the thinned jaw effective portion as for width, as well as reliable grasping and holding of tissues, while the remaining part of the forceps retains its compactness, convenience in its application is ensured and a comparatively small weight of the forceps as a whole is provided.

It is expedient that the surface of transition from the narrower jaw effective portion to the remaining part of the jaws be situated closer to the end of the effective portion than the surface of transition from the higher jaw effective portion at the base to the remaining part of the jaws. This feature makes it possible to provide the required rigidity of the forceps jaws with a comparatively small width of the jaw effective portion. In addition, such a mutual arrangement of said transition surfaces in relation to the locking element is more reasonable ergonomically.

Whenever a hinge joint is provided between the forceps halves with curved jaws whose effective portion makes up an angle with the plane square with the hinge joint axis, it is expedient that the surfaces of transition from the narrower jaw effective portion higher at the base, to the remaining portion of the jaws be located on the side of the hinge joint. Such a feature makes the forceps more maneuvrable in a narrow operative wound and adds to the convenience of manipulations with the instrument when bringing it to the place of compression of tissues and organs, e.g., in the small pelvis during proctologic surgery or operations on the esophagus.

The aforementioned construction features of the forceps enable one to extend their functional capabilities and to add to reliability of their practical application and to convenience in handling and maintenance.

BRIEF DESCRIPTION OF DRAWINGS

In what follows the present invention is illustrated by a detailed description of some specific though not limiting exemplary embodiments of its practical implementation to be read with reference to the accompanying drawings, wherein:

FIG. 1 is a schematic front view of surgical forceps, according to the invention;

FIG. 2 is a side of surgical forceps, according to the invention;

FIG. 3 is a scaled-up fragmentary view of the jaw effective portion, according to the invention;

FIG. 17 is a front view of surgical forceps, according to the invention, having curves jaws;

FIG. 18 is a side view of surgical forceps, according to the invention, having curved jaws; and FIG. 19 is a top view of surgical forceps, according to the invention, having curved jaws.

PREFERRED EMBODIMENT

Figure 4:
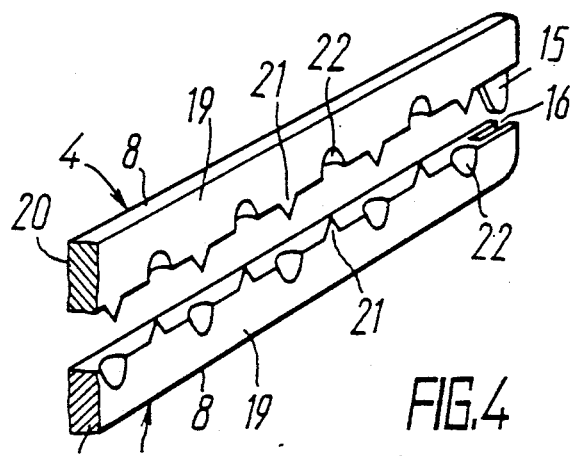
FIG. 4 is a stereoscopic view of the forceps jaw effective portion, according to the invention, showing prongs and recesses arranged on the side of one longitudinal edge of the jaw compressing surface.

The surgical forceps disclosed in this invention, are composed of two halves 1, 2 (FIG. 1) which are movably are interconnected. In a given specific embodiment considered hereinafter, such a movable connection is effected with the aid of a hinge joint 3 which provides a possibility of a mutual rotary motion of the halves 1 and 2. However, the halves 1, 2 of the forceps disclosed herein may be interlinked also with the aid of guides (not shown in the Drawing) which ensure parallel mutual travel of the halves. Each of the halves 1, 2 terminates in an oblong jaw 4 or 5, respectively and has a respective handle 6 or 7. Each of the jaws 4, 5 consists of an effective portion 8 and a remaining part 9 located between the effective portion 8 and the hinge joint 3. In the construction of the forceps represented in the Drawing the handles 6, 7 have ring-shaped grips 10 and are interlinked through a rack lock 11, while the halves 1, 2 are interconnected with the aid of a box lock 12 (FIG. 2). Ends 13 14 (FIG. 1) of the effective portion of the jaws 4, 5 of the forceps may have a projection 15 (FIG. 3) on one of the jaws, e.g., on the jaw 4, said projection being adapted to engage a recess 16 provided in the other jaw, e.g. in the jaw 5, both said projection and said recess serving to fix the jaws 4, 5 against mutual crosswise displacements.

Figure 5:
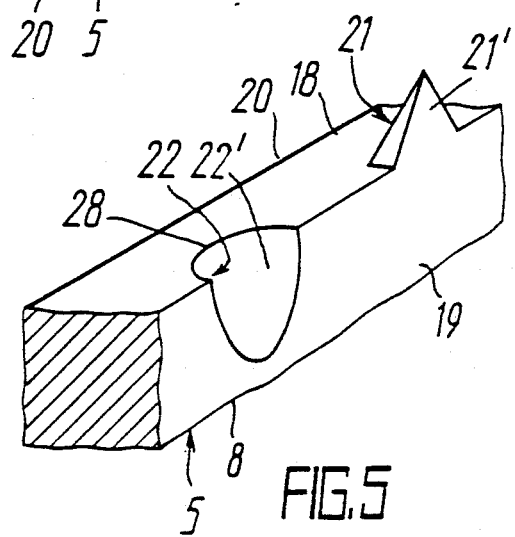
FIG. 5 is a scaled-up fragmentary view of the prongs and recesses on the effective portion of the jaws of the forceps of FIG. 4.

The jaws 4, 5 (FIG. 1) have on their effective portion 8 compressing surfaces 17, 18 (FIG. 4) and outer surfaces 19, 20. The compressing surfaces 17, 18 of the effective portion of each jaw carry alternating prongs 21 and recesses 22. The prongs 21 stand over the compressing surfaces 17, 18 and their points face the opposite jaw. The jaws 22 are interposed between the prongs 21 so that the prongs 21 of the jaw 4 are situated opposite to the recesses 22 of the jaw 5, and vice versa, the prongs 21 of the jaw 5 are located against the recesses 22 of the jaw 4. The prongs 21 and the recesses 22 may be arranged on one longitudinal edge of the compressing surfaces 17, 18 of the jaw effective portion, e.g., on the side of the outer surface 19 (FIGS. 4, 5). However, the prongs 21 and the recesses 22 may be arranged also on both longitudinal edges of the compressing surface, e.g., the surface 18 (FIG. 18) on the side of both outer surfaces 19, 20. The recesses 22 are open towards the outer surface 19 or 20 of the effective portion 8 of the jaws, e.g., the jaw 5. With the effective portions of the jaws 4 and 5 (FIGS. 3, 7 to 10) of the forceps brought together completely, the prongs 21 engage the recesses 22.

Figure 11:
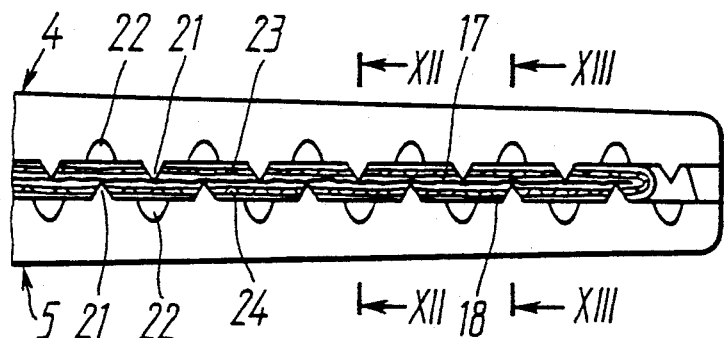
FIG. 11 is a section taken along the outside jaw surface to illustrate the walls of an organ while compressed by the effective portion of the forceps jaws.
Figure 12:
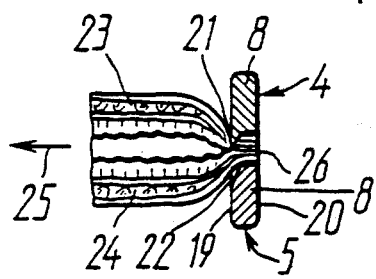
FIG. 12 is a section taken along the line XII—XII in FIG. 11.
Figure 13:
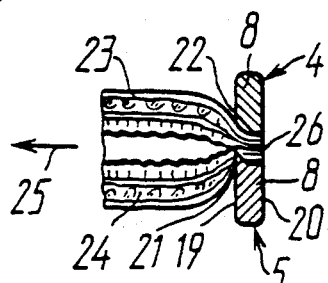
FIG. 13 is a section taken along the line XIII—XIII in FIG. 11.

The aforediscussed specific construction features of the forceps presented herein make it possible to make the jaw effective portion very narrow (practically half as wide as in the known forceps) and at the time ensure reliable grasping and fixing of walls 23, 24 (FIG. 11) of the organ being operated upon. Regardless the thickness of the walls (23, 24), when the latter are compressed between the jaws 4, 5 of the forceps the pointed prongs 21 stick into both of the walls 23, 24 so as to prevent said walls from escaping as a result of considerable tensioning of the tissues occurring in the direction facing an arrow 25 (FIGS. 12, 13). Reliable fixing of the tissues is provided even in the case where the compressed walls 23, 24 of the organ involved have been excised at the jaws (a tissue section 26) on the side of the outer surface 20 opposite to the prongs 21 and the recesses 22 arranged unilaterally on the side of the outer surface 19. Thanks to the aforesaid feature the forceps are efficacious when used in conjunction with suturing appliances for closing the cavity and fixing the resected portion of the organs, which is out off the remaining portion after a mechanical suture has been applied thereto. In the case of a bilateral arrangement of the prongs 21 and the recesses 22 (FIGS. 5, 9 10) the position of the tissue section 26 with respect to either of the outer surfaces 19 and 20 of the effective portion 8 is of no importance for ensuring reliable grasping and holding of the organ's walls. The narrow effective portion 8 (FIG. 2) of the jaws 4, 5 (FIG. 3) of the forceps enables one to attain good maneuvrability of the instrument in the operative wound. The recesses 22 (FIGS. 4, 5) that are open laterally and on the side of the compressing surface of the jaws, are convenient for cleaning the forceps, since they do catch blood clots and dirt and are easy to wash.

Figure 6:
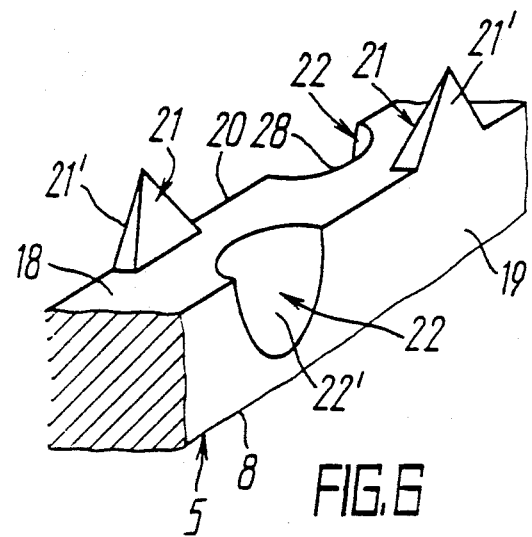
FIG. 6 is a stereoscopic fragmentary view of the effective portion of the forceps jaws, according to the invention, showing prongs and recesses arranged on the side of both longitudinal edges of the jaw compressing surface.
Figure 7:
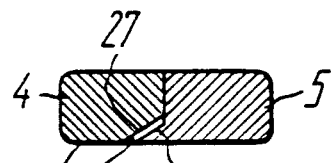
FIG. 7 is a section taken along the line VII—VII in FIG. 3 representing prongs and recesses arranged on the side of one longitudinal edge of the compressing surface of the jaw effective portion.
Figure 9:
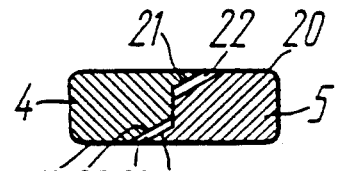
FIG. 9 is a section taken along the line IX—IX in FIG. 3 illustrating prongs and recesses arranged on the side of two longitudinal edges of the compressing surface of the jaw effective portion.
Figure 8:
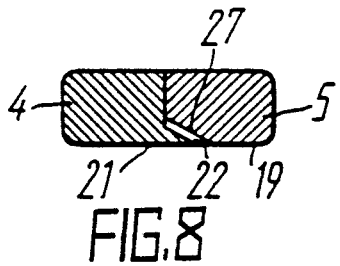
FIG. 8 is a section taken along the line VIII—VIII in FIG. 3 showing prongs and recesses arranged on the side of one longitudinal edge of the compressing surface of the jaw effective portion.
Figure 10:
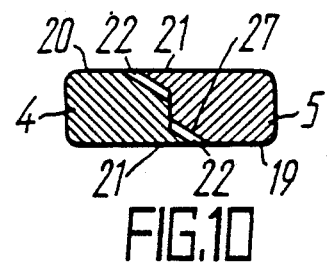
FIG. 10 is a section taken along the line X—X in FIG. 3 demonstrating prongs and recesses arranged on the side of two longitudinal edges of the compressing surface of the jaw effective portion.

A portion 21' (FIGS. 5, 6) of the lateral surface of the prongs 21 is in fact an extension to the outer surface 19 (or 20 in cases of a bilateral arrangement of the prongs as shown in FIG. 5) of the effective portion 8 (FIG. 1) of the jaws 4, 5. In a given specific embodiment of the forceps the prongs 21 (FIGS. 5, 6) are shaped as a pointed-vertex pyramid. The prongs 21 may, however, be shaped as a cone (not shown in the Drawing) dissected by a plane parallel to the cone axis. A surface 22' of the recess 22 is in fact a part of the surface of a body of revolution, a generant 27 (FIGS. 7 through 10) of said surface located in an axial section of the recess 22, being in an inclined position to the outer surface 19 or 20 of the jaw effective portion. The aforesaid feature makes it possible, with a relatively narrow width of the effective portion 8 (FIGS. 1, 2) of the forceps jaws 4, 5, to enhance the strength thereof, reduce the concentration of stresses nearby the recesses 22 (FIGS. 5, 6) when compressing the tissues and walls of organs, and provide better forceps cleaning conditions. The cross-section of the recess 22 is shaped as an arc 28. The prongs 21 and the recesses 22 are expedient to be spaced equidistantly along the jaw effective portion, while the recesses 22 are to be spaced half-pitch apart from the adjacent prongs 21.

According to an embodiment of the forceps having the prongs (FIG . 6) and the recesses 22 arranged along each of the edges of the compressing surface 18 of the jaw effective portion 8, said prongs 21 and recesses 22 on one edge located on the side of the outer surface 19, are displaced with respect to the prongs 21 and the recesses 22 located on the side of the outer surface 20. The amount of displacement of the like elements arranged along the both edges of the compressing surface of the jaw effective portion 8 is expedient to be equal to one half of the pitch, i.e., so that the prongs 21 and the recesses 22 should be positioned staggerwise. Such a construction arrangement of the effective portion 8 (FIG. 1) of the jaws 4, 5 adds to reliability of grasping the organ's walls due to closer location of pricks made by the prongs 21 (FIG. 6) are arranged not linearly but over an area limited to the width of the effective portion 8 of the forceps jaws (e.g., the jaw 5). Displacement of the prongs 21 on one edge of the compressing surface 18 of the effective portion 8 of the jaw 5 with respect to the prongs 21 on the other edge exposes the compressing surface 18 of the jaw 5 at the base of the prongs 21, which is more favourable from the standpoint of cleaning the forceps compared with the case where the prongs are arranged in opposition to one another. The corresponding longitudinal displacement of the recesses in their rows in more beneficial from the viewpoint of strength and rigidity of the effective portion 8 of the jaw 5 (or 4) which is important in view of inconsiderable width of the jaws.

Figures 14, 15:
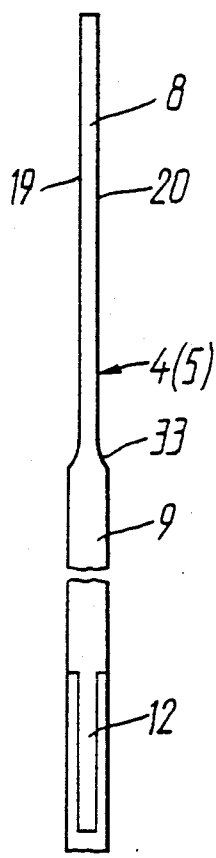
FIG. 14 is a fragmentary side view of the forceps, according to the invention.
FIG. 15 is a fragmentary side view of the forceps, according to the invention.
Figure 16:
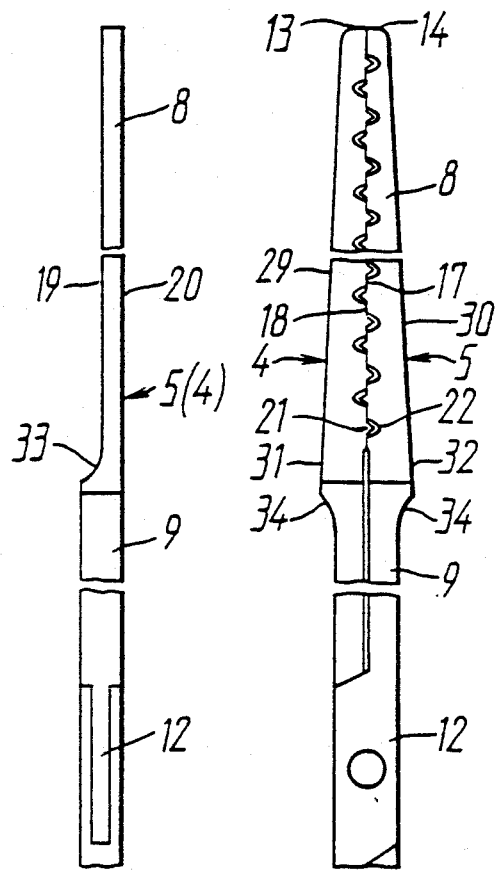
FIG. 16 is a fragmentary front view of the forceps embodiment illustrated in FIG. 5.

The effective portion 8 (FIGS. 2, 14, 15) of the forceps jaws 4, 5 is much narrower than the remaining portion 9 thereof. The outer surfaces 19, 20 of the effective portion 8 of the jaws 4, 5 are parallel to each other, whereas surfaces 29, 30 (FIGS. 1, 16) opposite to the compressing surfaces 17, 18 are so inclined that the height of the effective portion 8 of the jaws 4, 5 increases from the ends 13, 14 towards base 31, 32 of the effective portion which correspond approximately to the position of the last (from the ends) prong 21 or recess 22. The whole complex of the construction features considered hereinabove provides for equal conditions for compression, grasping and fixation of tissues and walls of organs by the prongs 21 along the entire length of the effective portion 8 of the jaws 4, 5 which features a comparatively small width and therefore requires but a relatively narrow area of tissues for setting the effective portion 8 of the jaws 4, 5. Besides, the required rigidity of the oblong remaining portion 9 of the jaws is ensured, as well as a possibility of employing the lock 12 and the rest of the forceps elements (i.e., the handles 6, 7, the rack lock 11, and other construction elements) unified and standardized as for shape and size for the various types of forceps featuring various dimensions of the jaw effective portion.

In order to attain the required rigidity of the effective portion 8 (FIGS. 15, 16) of the jaws 4, 5 featuring comparatively long length and aimed at compressing very dense and compact tissues and walls of relatively great length (e.g., when compressing and closing the cavity of the resected portion of the stomach after its stitching up with a mechanical suture applied with the aid of a suturing appliance, the length of said resected portion along the line of suture amounting to 100 mm and over), the height of the effective portion 8 of the jaws 4, 5 at the base 31, 32 (FIG. 16) exceeds that of the remaining portion 9. It is due to such a construction that, with the width of the effective portion 8 of the jaws 4, 5 less than the width of the remaining portion 9, the rest of the forceps elements remain compact, convenience in forceps application and a relatively low weight of the instrument as a whole are provided, as well as a possibility of unification and standardization of the forceps construction elements. A surface 33 (FIG. 15) of transition from the narrower effective portion 8 of the jaws 4, 5 to the remaining portion 9 is in this case located closer to the end 13, 14 of the effective portion 8 than a surface 34 (FIG. 16) of transition from the higher effective portion 8 at the base 31, 32 to the remaining portion 9 of the jaws 4, 5. The surfaces 33, 34 of transition are cylindrical-shaped in a given exemplary embodiment of the forceps.

The surgical forceps, according to the present invention, may have either straight or curved jaws.

According to one of the embodiments of the forceps featuring their halves 1, 2 (FIG. 1) interconnected through a hinge joint, the jaws 4, 5 are curved. The effective portion 8 (FIG. 18) of the jaws makes up an angle of, e.g., 90 degrees with a plane square with the axis of the hinge joint 3. The outer surface 20 of the effective portion 8 of the forceps jaws which is located on the outside of the hinge joint 3, has a long-sweep transit 35 at the bending point facing the remaining portion 9 of the jaws 4, 5, whereas a cylindrical surface 36 of transition from the narrower effective portion 8 to the remaining portion 9 with a projection 37 is located on the inner side. Respective surfaces 36 and 38 of transition from the narrower and the higher (at the base) effective portion 8 of the jaws 4, 5 to the remaining portion 9 are situated on the side of the hinge joint 3. Such a construction arrangement of the forceps having curved jaws (free from angulated projections imparts the effective portion 8 of the jaws 4, 5 compact, makes it more maneuvrable in a narrow operative wound renders the jaws adequately rigid. To compensate for elastic deformation of the cantilevered jaws 4, 5 (FIG. 19) of the forceps and to provide a uniform compression of tissues as for the length of the effective portion 8 of the jaws 4, 5 the latter are so made that, with the forceps in the initial position, i.e., when teeth 39 (FIG. 17) of the rack lock 11 of the forceps are engaged each other, the ends 13, 14 (FIG. 19) of the effective portion 8 of the jaws 4, 5 get in contact with each other, while at the base 31, 32 the jaws are space somewhat apart from each other. In the course of compression of tissues and walls of organs the angle of taper between the jaws 4, 5 decreases to zero.

The aforementioned FIGS. 1 through 9 illustrate various embodiments of the forceps disclosed in the invention, wherein both of the jaws 4, 5 (FIGS. 1, 3, 4, 11, 16) comprise the effective portion 8 having the prongs 21 and the recesses 22. It is, however, obvious that the forceps, according to the present invention, may be so embodied that the prongs 21 be provided on one of the jaws only, e.g., on the jaw 4, while the respective recesses 22 may be provided only on the opposite jaw, e.g., on the jaw 5 (not shown in the Drawing).

Besides, the effective portion 8 with the prongs 21 and the recesses 22 may be made not only straight but also curved, e.g., along an arc.

It is to be understood that the embodiments of the surgical forceps as discussed in the disclosure hereinabove and illustrated in the accompanying drawings should by no means be regarded as covering all practicable embodiments of the invention that could be found reasonable in surgical practice nowadays.

The herein-proposed surgical forceps operates as follows.

The tissues or walls 23, 24 (FIGS. 11 through 13) of the organ operated upon are compressed either atraumatically if said tissues or organ's walls are to be retained after surgery, or roughly taking no care of possible traumatic lesion of the tissues involved when the forceps is applied to the resected portion of the organ operated upon. Irrespective of the thickness of the organ's walls 23, 24 being compressed the prongs 21 (FIG. 11) of the effective portion 9 of the jaws 4, 5 stick into the walls 23, 24, thus fixing them reliably against slipping out of the space confined between the compressing surfaces 17, 18 (FIG.11) of the forceps jaws 4, 5.

When using for grasping and fixing tissues or the walls 23, 24 of an organ a forceps having a single row of the prongs 21 (FIGS.4, 5) and the recesses 22 arranged on the side of one of the outer surfaces, e.g., the surface 19, of the effective portion 8 of the jaws 4, 5, and the surgery involves excision of tissues along the forceps jaws, the forceps should be so positioned that the surface of the section 26 (FIGS. 12, 13) to be performed be located on the side opposite to the outer surface 19 of the effective portion 8 of the jaws 4, 5 corresponding to the prongs 21 and the recesses 22.

When using for grasping and fixing tissues or the walls 23, 24 of organs a forceps having two rows of the prongs 21 (FIG. 6) and the recesses 22 arranged on each side of the outer surface 19, 20 of the effective portion 8 of the forceps jaws 4, 5, and necessity arises in the course of surgery for excision of tissues along the forceps jaws the position of the latter with respect to the surface of the section (26) does not matter.

When using the present forceps in combination with a suturing appliance for compressing and fixing the resected portion of an organ, application of a mechanical suture (e.g., to the stomach in the case of gastrectomy), the resected portion of the organ is encompassed by the forceps jaws (not shown in the Drawings), the jaws are brought to contact with the branches of the suturing appliance, and the organ walls are compressed on the side of its resected portion. The small width of the effective portion 8 (FIGS. 2, 14, 15, 18) of the jaws 4, 5 provides for good maneuvrability of the present forceps during manipulations therewith and its convenient approach to the place of application of a mechanical suture. The prongs 21 (FIGS. 12, 13) and the recesses 22 of the forceps and located on the side opposite to the suturing appliance. Next the tissues are dissected, using a scalpel, between the forceps jaws 4, 5 and the suturing appliances. Then the staple magazine and the die of the suturing appliance are brought apart, thus releasing the organ stitched up with a mechanical suture. The forceps jaws 4, 5 close reliably the cavity of the resected portion of the organ, since the walls 23, 24 of the organ have been reliably grasped by the prongs 21 of the effective portion 8 and fixed against slipping out despite a comparatively small width of the effective portion 8 of the jaws 4, 5.

Industrial Applicability

Thus, the construction features of the surgical forceps, according to the invention, provide for the combination of good maneuvrability of the forceps under diverse conditions of its application in the course of surgery, and high-reliability grasping and fixing tissues and organ walls, strength of the jaws, service durability of the forceps as a whole, and convenience in handling and maintenance. These advantages make it possible to successfully use the forceps of the present invention (e.g., that with curved jaws) when manipulating deeply in a narrow operative wound, e.g., during surgery on the esophagus or in proctology, when reliable closure of the infected cavity of the rectal or colonic end is required, under conditions of a hindered access, after excision of the resected organ portion along the forceps jaws followed by holding the intestinal end with the closed cavity thereof during subsequent manipulations involved in, e.g., surgery for establishing coloproctostomy. The aforesaid advantages make the forceps applicable also in the cases where there is a deficit of tissue required for setting the forceps jaws at the place of grasping and fixing tissues. The advantages of the proposed forceps make also successfully applicable its various embodiments in conjunction with sutturing appliances for compressing the resected organ portion after application of a mechanical suture.

All these advantages enable one to improve the quality of surgery to simplify surgeon's work and that of attending personnel, extends the finctional capabilities of the forceps of the present type in diverse branches of surgery.

What is claimed is:

1. Surgical forceps comprising
   two movably interconnected halves, each of said halves terminating in an oblong jaw having an effective portion with a compressing surface, alternately arranged prongs and recesses aligned along at least one edge of said compressing surface of one jaw corresponding to respective recesses and prongs aligned along at least one edge on the compressing surface of the other jaw, said prongs and recesses being arranged on at least one longitudinal edge of the compressing surface with said recesses open towards a lateral side surface of the effective portion of the jaw.

2. Surgical forceps as claimed in claim 1, wherein a part of a lateral surface of said prong is an extension of the lateral side surface of the effective portion of said jaw.

3. Surgical forceps as claimed in claim 1, wherein a surface of said recess forms part of a surface of a body of revolution, a generant of said surface of the body of revolution is located in an axial section of said recess and is inclined with respect to the lateral side surface of the jaw effective portion.

4. Surgical forceps as claimed in claim 1, wherein with said prongs and said recesses arranged along each longitudinal edge of said compressing surface of the effective portion of the jaw, the prongs and recesses arranged on one longitudinal edge are displaced with respect to the prongs and recesses arranged on the opposite edge of the compressing surface of the effective portion of the jaw.

5. Surgical forceps as claimed in claim 1, wherein the width of the effective portion of said jaws is much smaller than the width of the remaining part of the jaws.

6. Surgical forceps as claimed in claim 5, wherein the height of the effective portion of said jaws rises from the end of said effective portion towards a base so that the height of the effective portion of the jaws at the base exceeds the height of the remaining part of the jaws.

7. Surgical forceps as claimed in claim 5, wherein the surface of transition from the narrower effective portion of said jaws to the remaining part of the jaws is situated closer to the end of said effective portion than the surface of transition from the higher effective portion of said jaws at a base to the remaining part of the jaws.

8. Surgical forceps as claimed in claim 7, wherein with said two halves having curved jaws interconnected through a hinge joint, said curved jaws having their effective portion arranged at an angle to the plane square with the axis of the hinge joint the surfaces of transition and from the narrower effective portion of said jaws, which is higher at a to the remaining portion of said jaws, are situated on the side of the hinge joint.

9. Surgical forceps comprising
   two movably interconnected halves, each of said halves terminating in an oblong jaw having an effective portion with two lateral outer surfaces and a compressing surface,
   alternatingly arranged prongs and recesses corresponding to respective recesses and prongs on the compressing surface of the other jaw,
   said prongs and said recesses being arranged on at least one longitudinal edge of the compressing jaw surface with said recesses opening towards the respective lateral outer surface adjoining the edge of said compressing surface having said alternating prongs and recesses.

10. Surgical forceps as claimed in claim 9, wherein a lateral surface of said prongs is an extension of a corresponding lateral outer surface of the effective portion of said jaw.

11. Surgical forceps as claimed in claim 9, wherein said recess includes a surface of a body of revolution, the generant of said surface is located in an axial section of said recess and is inclined with respect to an outer surface of the effective portion.

12. Surgical forceps as claimed in claim 9, wherein the prongs and recesses arranged on one longitudinal edge of the compressing surface are offset with respect to the prongs and recesses arranged on the opposite longitudinal edge of the compressing surface of the jaw effective portion.

13. Surgical forceps as claimed in claim 9, wherein the effective portion of said jaws is narrower than the remaining part of the jaws.

14. Surgical forceps as claimed in claim 13, wherein a height of the effective portion of said jaws rises from an end of said effective portion towards a base of said effective portion so that a height of the effective portion at the base exceeds the height of the remaining part of the jaws.

15. Surgical forceps as claimed in claim 13, wherein a surface of transition from the narrower effective portion of said jaws to the remaining part of the jaws is situated closer to the end of said effective portion than the surface of transition from the higher effective portion of said jaws at the base to the remaining part of the jaws.

16. Surgical forceps as claimed in claim 15, wherein said two halves include curved jaws interconnected through a hinge joint, said curved jaws having their effective portion arranged at an angle to a plane which is square with a hinge joint axis, the surfaces of transition from the narrower effective portion of said jaws which is higher at the base, to the remaining portion of said jaws, are situated on a side of the hinge joint.

* * * * *